(12) United States Patent
Lange et al.

(10) Patent No.: US 8,376,954 B2
(45) Date of Patent: Feb. 19, 2013

(54) TECHNIQUES FOR PREDICTION AND MONITORING OF RESPIRATION-MANIFESTED CLINICAL EPISODES

(75) Inventors: Daniel H. Lange, Kfar Vradim (IL); Yosef Gross, Moshav Mazor (IL); Avner Halperin, Ramat Gan (IL)

(73) Assignee: Earlysense Ltd., Ramat Gan (IL)

( * ) Notice: Subject to any disclaimer, the term of this patent is extended or adjusted under 35 U.S.C. 154(b) by 1839 days.

(21) Appl. No.: 11/446,281

(22) Filed: Jun. 2, 2006

(65) Prior Publication Data

US 2006/0224076 A1 Oct. 5, 2006

Related U.S. Application Data

(63) Continuation of application No. 11/048,100, filed on Jan. 31, 2005, now Pat. No. 7,077,810.

(60) Provisional application No. 60/541,779, filed on Feb. 5, 2004.

(51) Int. Cl.
*A61B 5/08* (2006.01)
(52) U.S. Cl. ......... 600/529; 600/534; 600/538; 600/484
(58) Field of Classification Search .......... 600/529–543, 600/484
See application file for complete search history.

(56) References Cited

U.S. PATENT DOCUMENTS

| | | | |
|---|---|---|---|
| 3,890,958 A | 6/1975 | Fister | |
| 4,122,838 A | 10/1978 | Leonard | |
| 4,301,879 A | 11/1981 | Dubow | |
| 4,338,950 A | 7/1982 | Barlow, Jr. | |
| 4,494,553 A | 1/1985 | Sciarra | |
| 4,657,025 A | 4/1987 | Orlando | |
| 4,657,026 A | 4/1987 | Tagg | |
| 4,686,999 A | 8/1987 | Snyder | |
| 4,738,264 A | 4/1988 | Orlando | |
| 4,757,825 A | 7/1988 | Diamond | |
| 4,817,610 A | 4/1989 | Lee | |
| 4,926,866 A | 5/1990 | Lee | |
| 5,002,060 A | 3/1991 | Nedivi | |
| 5,010,772 A | 4/1991 | Bourland | |
| 5,025,791 A | 6/1991 | Niwa | |
| 5,076,281 A | 12/1991 | Gavish | |
| 5,107,845 A * | 4/1992 | Guern et al. | 600/473 |
| 5,111,826 A | 5/1992 | Nasiff | |
| 5,137,033 A | 8/1992 | Norton | |

(Continued)

FOREIGN PATENT DOCUMENTS

| | | |
|---|---|---|
| EP | 0853918 A2 | 7/1998 |
| GB | 2329966 A1 | 4/1999 |

(Continued)

OTHER PUBLICATIONS

Kap-Ho Seo, et al., "Bed-type robotic system for the bedridden", Advanced Intelligent Mechatronics, Proceedings, 2005 IEE/ASME International Conference on Monterey, CA Jul. 24-28, 2005. Piscataway, NJ, USA pp. 1170-1175.

(Continued)

*Primary Examiner* — Navin Natnithithadha
(74) *Attorney, Agent, or Firm* — Rodney J. Fuller; Booth Udall Fuller, PLC

(57) ABSTRACT

A method is provided for predicting an onset of a clinical episode, the method including sensing breathing of a subject, determining at least one breathing pattern of the subject responsively to the sensed breathing, comparing the breathing pattern with a baseline breathing pattern, and predicting the onset of the episode at least in part responsively to the comparison. Other embodiments are also described.

36 Claims, 2 Drawing Sheets

U.S. PATENT DOCUMENTS

| | | | | |
|---|---|---|---|---|
| 5,235,989 A | | 8/1993 | Zomer | |
| 5,253,656 A | | 10/1993 | Rincoe | |
| 5,276,432 A | | 1/1994 | Travis | |
| 5,309,921 A | * | 5/1994 | Kisner et al. | 600/532 |
| 5,309,922 A | | 5/1994 | Schechter | |
| 5,319,363 A | | 6/1994 | Welch | |
| 5,368,026 A | | 11/1994 | Swedlow | |
| 5,393,935 A | | 2/1995 | Hasty | |
| 5,448,996 A | | 9/1995 | Bellin et al. | |
| 5,479,939 A | | 1/1996 | Ogino | |
| 5,515,865 A | | 5/1996 | Scanlon | |
| 5,520,176 A | | 5/1996 | Cohen | |
| 5,522,382 A | | 6/1996 | Sullivan et al. | |
| 5,540,734 A | | 7/1996 | Zabara | |
| 5,590,650 A | | 1/1997 | Genova | |
| 5,684,460 A | | 11/1997 | Scanlon | |
| 5,687,734 A | | 11/1997 | Dempsey | |
| 5,699,038 A | | 12/1997 | Ulrich | |
| 5,730,140 A | | 3/1998 | Fitch | |
| 5,738,102 A | | 4/1998 | Lemelson | |
| 5,743,263 A | | 4/1998 | Baker, Jr. | |
| 5,797,852 A | | 8/1998 | Karakasoglu | |
| 5,800,337 A | | 9/1998 | Gavish | |
| 5,800,360 A | * | 9/1998 | Kisner et al. | 600/532 |
| 5,853,005 A | | 12/1998 | Scanlon | |
| 5,879,313 A | | 3/1999 | Raviv et al. | |
| 5,902,250 A | | 5/1999 | Verrier et al. | |
| 5,944,680 A | | 8/1999 | Christopherson et al. | |
| 5,957,861 A | | 9/1999 | Combs | |
| 5,964,720 A | | 10/1999 | Pelz | |
| 5,989,193 A | | 11/1999 | Sullivan | |
| 6,014,346 A | | 1/2000 | Malone | |
| 6,015,388 A | | 1/2000 | Sackner et al. | |
| 6,033,370 A | | 3/2000 | Reinbold et al. | |
| 6,036,660 A | | 3/2000 | Toms | |
| 6,047,203 A | | 4/2000 | Sackner et al. | |
| 6,062,216 A | * | 5/2000 | Corn | 128/204.23 |
| 6,064,910 A | | 5/2000 | Andersson et al. | |
| 6,090,037 A | | 7/2000 | Gavish | |
| 6,093,146 A | | 7/2000 | Filangeri | |
| 6,104,949 A | | 8/2000 | Pitts Crick | |
| 6,126,595 A | | 10/2000 | Amano et al. | |
| 6,134,970 A | | 10/2000 | Kumakawa | |
| 6,135,970 A | | 10/2000 | Kadhiresan et al. | |
| 6,157,850 A | | 12/2000 | Diab | |
| 6,168,568 B1 | | 1/2001 | Gavriely | |
| 6,198,394 B1 | | 3/2001 | Jacobsen | |
| 6,223,064 B1 | | 4/2001 | Lynn et al. | |
| 6,239,706 B1 | | 5/2001 | Yoshiike et al. | |
| 6,259,355 B1 | | 7/2001 | Chaco | |
| 6,261,238 B1 | | 7/2001 | Gavriely | |
| 6,290,654 B1 | | 9/2001 | Karakasoglu | |
| 6,325,761 B1 | | 12/2001 | Jay | |
| 6,352,517 B1 | | 3/2002 | Flock et al. | |
| 6,368,287 B1 | | 4/2002 | Hadas | |
| 6,375,621 B1 | | 4/2002 | Sullivan | |
| 6,375,623 B1 | | 4/2002 | Gavriely | |
| 6,383,142 B1 | | 5/2002 | Gavriely | |
| 6,402,691 B1 | | 6/2002 | Peddicord | |
| 6,409,661 B1 | | 6/2002 | Murphy | |
| 6,436,057 B1 | | 8/2002 | Goldsmith et al. | |
| 6,450,957 B1 | | 9/2002 | Yoshimi et al. | |
| 6,454,719 B1 | | 9/2002 | Greenhut | |
| 6,468,234 B1 | | 10/2002 | Van der Loos et al. | |
| 6,485,441 B2 | | 11/2002 | Woodward | |
| 6,498,652 B1 | | 12/2002 | Varshneya | |
| 6,512,949 B1 | | 1/2003 | Combs et al. | |
| 6,517,497 B2 | | 2/2003 | Rymut et al. | |
| 6,527,729 B1 | | 3/2003 | Turcott | |
| 6,544,173 B2 | | 4/2003 | West | |
| 6,544,174 B2 | | 4/2003 | West | |
| 6,547,743 B2 | | 4/2003 | Brydon | |
| 6,551,252 B2 | | 4/2003 | Sackner | |
| 6,561,978 B1 | | 5/2003 | Conn | |
| 6,579,232 B2 | | 6/2003 | Sakamaki | |
| 6,585,645 B2 | | 7/2003 | Hutchinson | |
| 6,589,188 B1 | | 7/2003 | Street et al. | |
| 6,599,251 B2 | | 7/2003 | Chen et al. | |
| 6,600,949 B1 | | 7/2003 | Turcott | |
| 6,616,606 B1 | | 9/2003 | Petersen | |
| 6,630,568 B1 | | 10/2003 | Johnson | |
| 6,631,281 B1 | | 10/2003 | Kastle | |
| 6,641,542 B2 | | 11/2003 | Cho et al. | |
| 6,646,556 B1 | | 11/2003 | Smith | |
| 6,662,032 B1 | | 12/2003 | Gavish et al. | |
| 6,666,830 B1 | | 12/2003 | Lehrman et al. | |
| 6,719,708 B1 | | 4/2004 | Jansen | |
| 6,731,311 B2 | | 5/2004 | Bufe | |
| 6,745,060 B2 | | 6/2004 | Diab | |
| 6,751,498 B1 | | 6/2004 | Greenberg et al. | |
| 6,752,766 B2 | | 6/2004 | Kowallik et al. | |
| 6,754,516 B2 | | 6/2004 | Mannheimer | |
| 6,790,183 B2 | | 9/2004 | Murphy | |
| 6,821,258 B2 | | 11/2004 | Reed | |
| 6,822,564 B2 | | 11/2004 | Al-Ali | |
| 6,830,548 B2 | | 12/2004 | Bonnet et al. | |
| 6,840,907 B1 | | 1/2005 | Brydon | |
| 6,856,141 B2 | | 2/2005 | Ariav | |
| 6,878,121 B2 | | 4/2005 | Krausman | |
| 6,893,404 B2 | | 5/2005 | Ragnarsdottir | |
| 6,955,647 B2 | | 10/2005 | Rice | |
| 6,980,679 B2 | | 12/2005 | Jeung | |
| 6,984,207 B1 | | 1/2006 | Sullivan | |
| 6,984,993 B2 | | 1/2006 | Ariav | |
| 6,988,989 B2 | | 1/2006 | Weiner | |
| 7,022,072 B2 | | 4/2006 | Fox | |
| 7,025,729 B2 | | 4/2006 | de Chazal | |
| 7,077,810 B2 | * | 7/2006 | Lange et al. | 600/538 |
| 7,079,035 B2 | | 7/2006 | Bock | |
| 7,283,161 B2 | | 10/2007 | Someya | |
| 7,304,580 B2 | | 12/2007 | Sullivan | |
| 7,314,451 B2 | * | 1/2008 | Halperin et al. | 600/534 |
| 7,390,299 B2 | | 6/2008 | Weiner | |
| 7,396,331 B2 | * | 7/2008 | Mack et al. | 600/300 |
| 7,396,333 B2 | * | 7/2008 | Stahmann et al. | 600/529 |
| 7,415,297 B2 | | 8/2008 | Al-Ali | |
| 7,428,468 B2 | | 9/2008 | Takemura | |
| 7,431,700 B2 | * | 10/2008 | Aoki et al. | 600/534 |
| 7,433,827 B2 | | 10/2008 | Rosenfeld | |
| 7,439,856 B2 | | 10/2008 | Weiner | |
| 7,454,359 B2 | | 11/2008 | Rosenfeld | |
| 7,508,307 B2 | | 3/2009 | Albert | |
| 7,572,225 B2 | * | 8/2009 | Stahmann et al. | 600/484 |
| 7,610,094 B2 | * | 10/2009 | Stahmann et al. | 607/42 |
| 7,629,890 B2 | | 12/2009 | Sullivan | |
| 7,666,151 B2 | | 2/2010 | Sullivan | |
| 7,689,440 B2 | | 3/2010 | Brown | |
| 7,704,215 B2 | | 4/2010 | Lewicke | |
| 7,778,851 B2 | | 8/2010 | Schoenberg | |
| 7,880,606 B2 | | 2/2011 | Al-Ali | |
| 7,896,813 B2 | | 3/2011 | Sowelam | |
| 7,938,782 B2 | * | 5/2011 | Stahmann et al. | 600/536 |
| 7,952,475 B2 | | 5/2011 | Ivanov | |
| 7,959,574 B2 | | 6/2011 | Bardy | |
| 2002/0058155 A1 | | 5/2002 | Guofang | |
| 2002/0077554 A1 | | 6/2002 | Schwartz | |
| 2002/0082486 A1 | | 6/2002 | Lavery | |
| 2002/0086870 A1 | | 7/2002 | Radulovacki | |
| 2002/0097155 A1 | | 7/2002 | Cassel | |
| 2002/0106709 A1 | | 8/2002 | Potts | |
| 2002/0196148 A1 | | 12/2002 | Nunome | |
| 2003/0004423 A1 | | 1/2003 | Lavie et al. | |
| 2003/0045806 A1 | | 3/2003 | Brydon | |
| 2003/0125612 A1 | | 7/2003 | Fox | |
| 2003/0135127 A1 | | 7/2003 | Sackner et al. | |
| 2003/0139678 A1 | | 7/2003 | Hoium | |
| 2003/0144829 A1 | | 7/2003 | Geatz | |
| 2003/0153831 A1 | | 8/2003 | Zumeris et al. | |
| 2003/0199945 A1 | | 10/2003 | Ciulla | |
| 2004/0010202 A1 | | 1/2004 | Nakatani | |
| 2004/0073098 A1 | | 4/2004 | Geva et al. | |
| 2004/0082874 A1 | * | 4/2004 | Aoki et al. | 600/534 |
| 2004/0111040 A1 | | 6/2004 | Ni | |
| 2004/0111045 A1 | | 6/2004 | Sullivan | |
| 2004/0116784 A1 | | 6/2004 | Gavish | |
| 2004/0133079 A1 | | 7/2004 | Mazar et al. | |
| 2004/0210155 A1 | | 10/2004 | Takemura et al. | |

| | | | |
|---|---|---|---|
| 2004/0225226 | A1 | 11/2004 | Lehrman et al. |
| 2004/0230105 | A1 | 11/2004 | Geva et al. |
| 2005/0043644 | A1 | 2/2005 | Stahmann et al. |
| 2005/0061315 | A1 | 3/2005 | Lee et al. |
| 2005/0074361 | A1 | 4/2005 | Tanoshima |
| 2005/0085734 | A1 | 4/2005 | Tehrani |
| 2005/0085866 | A1 | 4/2005 | Tehrani |
| 2005/0096557 | A1 | 5/2005 | Vosburgh |
| 2005/0119586 | A1 | 6/2005 | Coyle |
| 2005/0124864 | A1 | 6/2005 | Mack et al. |
| 2005/0165284 | A1 | 7/2005 | Gefen |
| 2005/0168341 | A1 | 8/2005 | Reeder |
| 2005/0192508 | A1 | 9/2005 | Lange et al. |
| 2005/0201970 | A1 | 9/2005 | Hu |
| 2005/0240091 | A1 | 10/2005 | Lynn |
| 2006/0028350 | A1 | 2/2006 | Bhai |
| 2006/0084848 | A1 | 4/2006 | Mitchnick |
| 2006/0129047 | A1 | 6/2006 | Ruotoistenmaki |
| 2006/0152378 | A1 | 7/2006 | Lokhorst |
| 2006/0224076 | A1 | 10/2006 | Lange |
| 2006/0241510 | A1 | 10/2006 | Halperin |
| 2007/0024451 | A1 | 2/2007 | Albert |
| 2007/0118054 | A1 | 5/2007 | Pinhas |
| 2007/0139678 | A1 | 6/2007 | Horita |
| 2007/0156031 | A1 | 7/2007 | Sullivan |
| 2007/0177785 | A1 | 8/2007 | Raffy |
| 2007/0249952 | A1 | 10/2007 | Rubin |
| 2007/0257564 | A1 | 11/2007 | Kitade |
| 2007/0276202 | A1 | 11/2007 | Raisanen |
| 2008/0004904 | A1 | 1/2008 | Tran |
| 2008/0005838 | A1 | 1/2008 | Wan Fong |
| 2008/0114260 | A1 | 5/2008 | Lange |
| 2008/0269625 | A1 | 10/2008 | Halperin |
| 2008/0275349 | A1 | 11/2008 | Halperin |
| 2009/0299229 | A1 | 12/2009 | Johnson |
| 2010/0215074 | A1 | 8/2010 | Lozinski |
| 2010/0234705 | A1 | 9/2010 | Lynn |

FOREIGN PATENT DOCUMENTS

| | | | |
|---|---|---|---|
| JP | 5323635 | A2 | 12/1993 |
| JP | 08-080285 | A2 | 3/1996 |
| JP | 08-225210 | A2 | 9/1996 |
| JP | 2001-037739 | A2 | 2/2001 |
| JP | 2001-145605 | A1 | 5/2001 |
| JP | 2002-336207 | A2 | 11/2002 |
| JP | 2003-225210 | A2 | 8/2003 |
| JP | 2004-049388 | A2 | 2/2004 |
| JP | 2005-021450 | A2 | 1/2005 |
| JP | 2005-095307 | A2 | 4/2005 |
| JP | 2005-143661 | A2 | 6/2005 |
| JP | 2005-160876 | A2 | 6/2005 |
| JP | 2005-279113 | A2 | 10/2005 |
| WO | 86/05965 | A2 | 10/1986 |
| WO | 96/08197 | A2 | 3/1996 |
| WO | 97/40748 | A2 | 11/1997 |
| WO | 99/04691 | A2 | 2/1999 |
| WO | 99/32537 | A2 | 7/1999 |
| WO | 01/80727 | A2 | 1/2001 |
| WO | 01/73718 | A2 | 10/2001 |
| WO | 03/013355 | A2 | 2/2003 |
| WO | WO-03/057025 | | 7/2003 |
| WO | 2004/091378 | A2 | 10/2004 |
| WO | WO-2004/114193 | | 12/2004 |
| WO | WO-2005/028029 | | 3/2005 |
| WO | WO-2005/037077 | | 4/2005 |
| WO | WO-2005/037366 | | 4/2005 |
| WO | 2005/055824 | A1 | 6/2005 |
| WO | 2005/074361 | A2 | 8/2005 |
| WO | WO-2006/008743 | | 1/2006 |
| WO | WO-2006/054306 | | 5/2006 |
| WO | WO-2006/082589 | | 8/2006 |
| WO | 2006/137067 | A2 | 12/2006 |
| WO | 2007/052108 | A2 | 5/2007 |
| WO | 09/138976 | A2 | 11/2009 |

OTHER PUBLICATIONS

Alihanka J et al., "A static charge sensitive bed. A new method for recording body movements during sleep", Electroencephalography and Clinical Neurophysiology, Elsevier, vol. 46, No. 6, Jun. 1, 1979, pp. 731-734.

Tamura T et al., "A system for monitoring temperature distribution in bed and its application to the assessment of body movement", Physiological Measurement, Institute of Physics ublishing, Bristol, GB, Vo. 14, No. 1, Feb. 1, 1993, pp. 33-41.

U.S. Appl. No. 60/504,229, Stahmann et al.

Shochat, Michael, et al., "PedemaTOR: Innovative Method for Detecting Pulmonary Edema at the Pre-Clinical Stage", http://www.isramed.info/rsmm_rabinovich/pedemator.htm.

Stegmaier-Stracca, Peter A., et al., "Cough Detection Using Fuzzy Classification", Proceedings of the 1995 ACM Symposium on Applied Computing, Nashville, TN, pp. 440-444.

Mack, David, et al., "Non-Invasive Analysis of Physiological Signals: NAPS: A low cost, passive monitoring for sleep quality and related applications" University of Virginia Health System.

Brenner,. Barry E., et al., "The Clinical Presentation of Acute Asthma in Adults and Children", In Brenner, BE, ed. Emergency Asthma (New York: Marcel Dekker, 1999, pp. 201-232.

"Non-Invasive Fiber-Optic Sensor Technology for Monitoring Sleep Apnea and SIDS", http://www.kidsource.com/products/flber.optic.SIDS.html.

"Breathing Easier with Asthma", pp. 1-46, http://www.ihc.com/xp/ihc/documents/clinica1/101/3/1/asthma_breathe.pdf.

Mintzer, Rich, "What the Teacher Should Know About Asthma Attacks", http://www.familyeducation.com/article/print/0,1303,65-415,00.html?obj_gra.

Poteet, Jackie, "Asthma", http://www.nku.edu/~rad350/asthmajp.html.

"Signs and symptoms of Asthma", http://www.indianchestsociety.org/symptomsofasthma.htm.

"Peak Flow Learning Center", http://www.njc.org/disease-info/diseases/asthma/living/tools/peak/index/aspx.

"Managing Asthma", http://kidshealth.org/pageManager.jsp?dn=KidsHealth&lic=1&ps=107&cat_id=143&article_set=2.

International Search Report of PCT/IL2011/050045 dated Jul. 13, 2012.

Bentur, L., et al., "Wheeze monitoring in children for assessment of nocturnal asthma and response to therapy", Eur. Respir. J., 2003, vol. 21, pp. 621-626.

Waris, M., et al., "A new method for automatic wheeze detection", Technology and Health Care, 1998, vol. 6, pp. 33-40.

Alihanka, J., et al., "A new method for long-term monitoring of the ballistocardiogram, heart rate, and respiration", Am. J. Physiol. Regul. Integr. Comp. Physiol., 1981, vol. 240, pp. 384-392.

Chang, A. B., et al., "Cough, airway inflammation, and mild asthma exacerbation", Archives of Disease in Childhood, 2002, vol. 86, pp. 270-275.

Korpas, J., et al., "Analsys of the cough sound: an overview", Pulmonary Pharmacology, 1996, vol. 9, pp. 261-268.

"British Guideline on the Management of Asthma: A national clinical guideline", British Thoracic Society, Scottish Intercollegiate Guidelines Network, Revised edition, Apr. 2004.

Brenner, Barry E., et al., "The Clinical Presentation of Acute Asthma in Adults and Children", In Brenner, BE, ed. Emergency Asthma (New York: Marcel Dekker, 1999, pp. 201-232.

Baren, Jill M., et al., "Current Concepts in the ED Treatment of Pediatric Asthma", Respiratory Medicine Consensus Reports (Thomson American Health Consultants, Dec. 28, 2003).

Plaut, Thomas F., "Tracking and treating asthma in young children", J. Respir. Dis. Pediatrician, 2003, vol. 5, No. 2, pp. 67-72.

Hsu, J. Y., et al., "Coughing frequency in patients with persistent cough: assessment using a 24 hour ambulatory recorder", Eur Respir J, 1994, vol. 7, pp. 1246-1253.

Salmi, Tapani, et al., "Long-term Recording and Automatic Analysis of Cough Using Filtered Acoustic Signals and Movements on Static Charge Sensitive Bed", Chest, 1988, vol. 94, pp. 970-975.

Van Der Loos, H. F. M., et al., "Development of Sensate and Robotic Bed Technologies for Vital Signs Monitoring and Sleep Quality Improvement", Abstract, Autonomous Robots, Jul. 2003, vol. 15, No. 1, http://www.ingenta.com/isis/searching/Expand/ingenta?pub=in fobike://klu/auro/2003/00000015/00000001/05126829.

Van Der Loos, H. F. Machiel, et al., "Unobstrusive Vital Signs Monitoring From a Multisensor Bed Sheet", RESNA'2001, Reno, NV, Jun. 22-26, 2001.

Pirrila, P., et al., "Objective assessment of cough", Eur Respir J, 1995, vol. 8, pp. 1949-1956.

International Search Report; PCT Application No. PCT/IL2005/000113 dated Nov. 15, 2005.

"Does my child have asthma?" Solano Asthma Coalition, American Lung Association of the East Bay (http://www.alaebay.org/misc_pdf/solano_asthma_coalition_child_asthma.pdf) (2001).

Medical Mutual clinical practice guidelines for asthma: 2004, Medical Mutual (Cleveland, OH), (http://www.medmutual.com/provider/pdf/resources/asthma4.pdf).

Ancoli-Israel S. et al., "The role of actigraphy in the study of sleep and circadian rhythms", Sleep, 26(3):342-392 (2003).

Bilmes et al., "A gentle tutorial of the EM algorithm and its application to parameter estimation for caussian mixture and hidden markov models", Internation Computer Science Institut, pp. 1-13 (1998).

Butter CD. et al., "Fiber optics strain gauge", Appl Opt., 17(18): 2867-2869 (1978).

Chaboyer W et al., "Predictors of adverse events in patients after discharge from the intensive care unit", Am J Crit Care, 17:255.263 (2008).

Delmore G. et al., "The role of augmented breaths (sighs) in bronchial asthma attacks", Pflugers Arch., 372(1):1-6 (1977).

Dempster AP. et al., "Maximum likelihood from incomplete data via the EM algorithm", Journal of the Royal Statistical Society, 39(1):1-38 (1977).

Fieselmann JF et al., "Respiratory rate predicts cardiopulmonary arrest for internal medicine inpatients", J Gen Intern Med, 8(7):354-360 (1993).

Fitzpatrick MF. et al., "Morbidity in nocturnal asthma: sleep quality and daytime cognitive performance", Thorax., 46(8):569-573 (1991).

Fitzpatrick, MF. et al., "Snoring, asthma and sleep disturbances in Britain: a community based survey", ERS Journal Ltd., pp. 531-535 (1993).

Hark et al., "Spontaneous sigh rates during sedentary activity: watching television vs reading", Ann Allergy Asthma Immunol., 94(2):247-250 (2005).

Hogan J., "Why don't nurses monitor the respiratory rates of patients?", Br J Nurs, 15(9):4894-92 (2006).

Hori et al., "Proposed supplements and amendments to 'A Manual of Standardized Terminology, Techniques and Scoring System for Sleep Stages of Human Subjects', the Rechtschaffen & Kales (1968) standard", Psychiatry Clin Neurosci., 55(3):305-310 (2001).

Hudgel et al., "Mechanics of the respiratory system and breathing pattern during sleep in normal humans", J Appl Physiol., 56(1): 133-137 (1984).

Jobanputra et al., "Management of acute asthma attacks in general practice", Br J Gen Pract., 41(351):410-413 (Oct. 1991).

Kandtelhardt, J.W. et al., "Breathing during REM and non-REM sleep: correlated versus uncorrelated behavior," 25 Physica. A., vol. 319, pp. 447-457, 2003.

Kapsali et al., "Potent bronchoprotective effect of deep inspiration and its absence in asthma", J Appl Physiol., 89(2):711-720 (2000).

Katz et al., "Detection of preterm labor by ambulatory monitoring of uterine activity: a preliminary report", Obstet Gynecol., 68(6): 773-778 (Dec. 1986).

Li, Q. and A. Barron, "Mixture density estimation," Advances in neural information processing systems, vol. 12, pp. 279-285, MIT press, 2000.

Lim To. et al., "Morbidity associated with asthma and audit of asthma treatment in out-patient clinics", Singapore Med J., 33(2):174-176 (1992).

Madge PJ et al., "Home nebuliser use in children with asthma in two Scottish Health Board Areas", Scott Med J., 40(5):141-143 (1995).

O'Connor CJ et al, "Identification of endotracheal tube malpositions using computerized analysis of breath sounds via electronic stethoscopes," Anesth Analg, 101:735-739 (2005).

Salmi et al., "Automatic analysis of sleep records with static charge sensitive bed", Electroencephalography and Clinical Neurophysiology, pp. 84-87 (1986).

Schwarz, "Estimating the dimension of a model", The Annals of Statistics, 6(2):461-464 (1978).

Shinar Z. et al., "Automatic detection of flow-wave-sleep using heart rate variability", Computers in cardiology, 28:593-596 (2001).

Sorvoja, H. And Myllyla, R., "Noninvasive blood pressure measurement methods," Molecular and Quantum Acoustics. vol. 27, 2006.

Thorpe C.W. et al., "Towards a quantitative description of asthmatic cough sounds", Eur Respir J, 5(6):685-692 (1992).

Van Hirtum A. et al., "Autoregressive acoustical modeling of free field cough sound", Proc Int Conference on Acoustics, Speech and Signal Processing, col. 1, pp. 493-496, Orlando, USA (2002).

Watanabe et al., "Noncontact method for sleep stage estimation", IEEE transactions on Biomedical Engineering 10 (51):1735-1748 (2004).

Whitney, C.W., et al., "Reliability of scoring respiratory disturbance indices and sleep staging," Sleep, 21(7):749-757 (Nov. 2, 1998).

Yongjoon et al., "Air matters sensor system with balancing tube for unconstrained measurement of respiration and heart beat movements", Physiol Meas, pp. 413-422 (Abstract only) (2005).

Oppenheim, A., and Schafer, R., "Discrete—Time Signal Processing", Prentice5' Hall, 1989, pp. 311-312 (1989).

Staderini, Enrico M., "UWB Radars in Medicine", IEEE Aerospace and Electronic Systems Magazine, 17(1)13-18 (2002).

Yien, HW et al., "Spectral analysis of systemic arterial pressure and heart rate signals as a prognostic tool for the prediction of patient outcome in the intensive care unit", Crit Care Med., 25(2):258-266 (1997).

Corresponding European Patent Application No. 12168737 European Search Report Sep. 3, 2012.

* cited by examiner

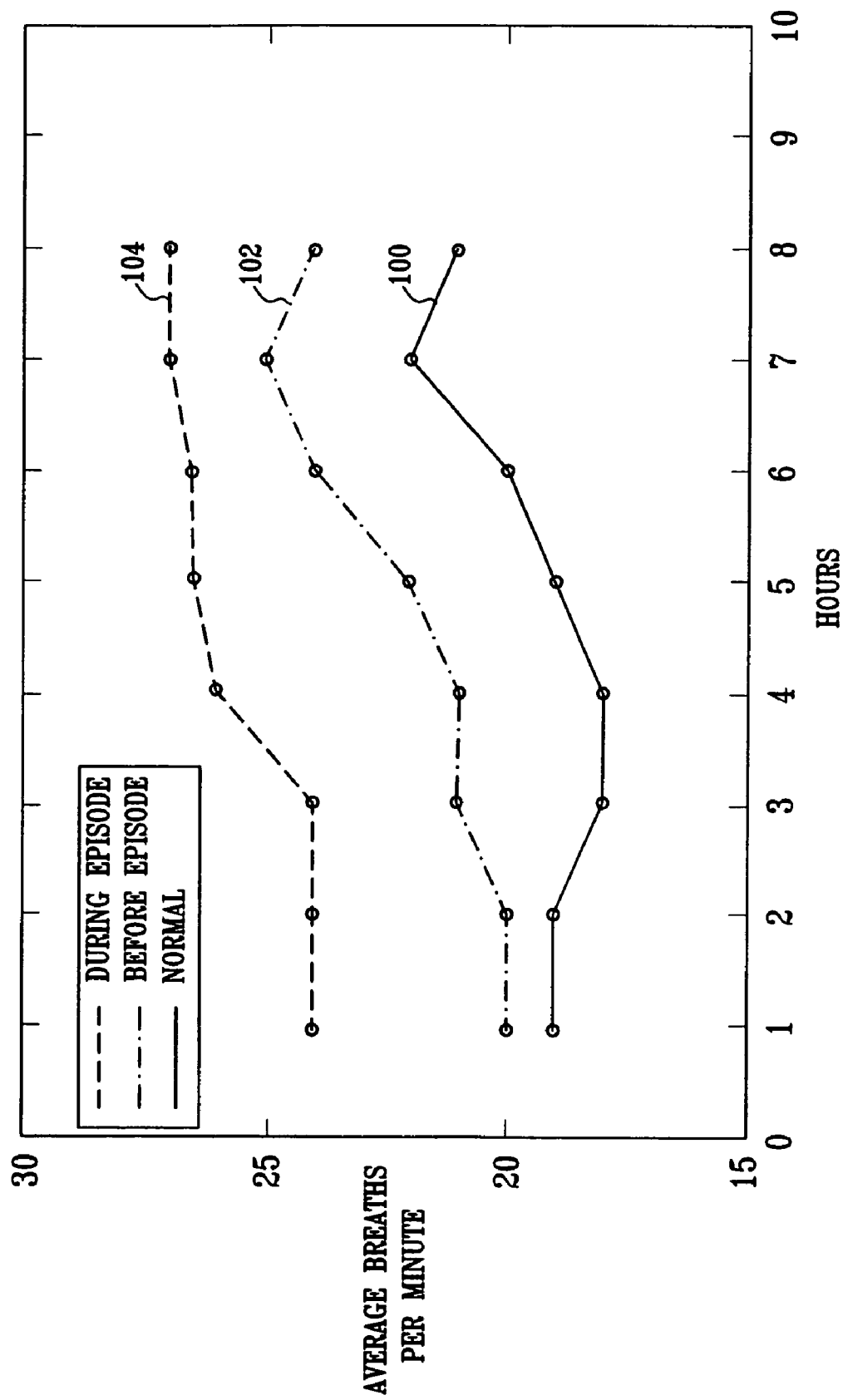

TECHNIQUES FOR PREDICTION AND MONITORING OF RESPIRATION-MANIFESTED CLINICAL EPISODES

CROSS-REFERENCES TO RELATED APPLICATIONS

This application claims the benefit of U.S. Provisional Patent Application 60/541,779, filed Feb. 5, 2004, entitled, "Method and apparatus for prediction and monitoring of respiration manifested clinical episodes," which is assigned to the assignee of the present application and is incorporated herein by reference.

This application is related to a PCT patent application filed on even date herewith, entitled, "Techniques for prediction and monitoring of respiration-manifested clinical episodes," which is assigned to the assignee of the present patent application and is incorporated herein by reference.

FIELD OF THE INVENTION

The present invention relates generally to predicting and monitoring abnormal physiological conditions, and specifically to methods and apparatus for predicting and monitoring abnormal physiological conditions by measuring and analyzing characteristics of respiration.

BACKGROUND OF THE INVENTION

Chronic diseases are often expressed by episodic worsening of clinical symptoms. Preventive treatment of chronic diseases reduces the overall dosage of required medication and associated side effects. Generally, preventive treatment should be initiated or intensified as soon as the earliest clinical symptoms are detected, in order to prevent progression and worsening of the clinical episode and to stop and reverse the pathophysiological process. Therefore, an ability to accurately monitor pre-episodic indicators increases the effectiveness of preventive treatment of chronic diseases.

Many chronic diseases interfere with normal breathing patterns, through a variety of physiological mechanisms. Common respiratory disorders, such as asthma, chronic obstructive pulmonary disease (COPD), and cystic fibrosis (CF), are direct modifiers of breathing patterns. Other chronic diseases, such as diabetes, epilepsy, and certain heart diseases, are also known to modify breathing activity, because of pathophysiologies leading to abnormal sympathetic and parasympathetic neural activity.

Asthma is a chronic disease with no known cure. Substantial alleviation of asthma symptoms is possible via preventive therapy, such as the use of bronchodilators and anti-inflammatory agents. Asthma management is aimed at improving the quality of life of asthma patients. Asthma management presents a serious challenge to the patient and physician, as preventive therapies require constant monitoring of lung function and corresponding adaptation of medication type and dosage. However, monitoring of lung function is not simple, and requires sophisticated instrumentation and expertise, which are generally not available in the non-clinical or home environment.

Monitoring of lung function is viewed as a major factor in determining an appropriate treatment, as well as in patient follow-up. Preferred therapies are based on aerosol-type medications to minimize systemic side-effects. The efficacy of aerosol type therapy is highly dependent on patient compliance, which is difficult to assess, further contributing to the importance of lung-function monitoring.

Asthma episodes usually develop over a period of several days, although they may sometimes seem to appear unexpectedly. The gradual onset of the asthmatic episode provides an opportunity to start countermeasures to stop and reverse the inflammatory process. Early treatment at the pre-episode stage may reduce the clinical episode manifestation considerably, and may even prevent the transition from the pre-clinical stage to a clinical episode altogether.

Two techniques are generally used for asthma monitoring. The first technique, spirometry, evaluates lung function using a spirometer, an instrument that measures the volume of air inhaled and exhaled by the lungs. Airflow dynamics are measured during a forceful, coordinated inhalation and exhalation effort by the patient into a mouthpiece connected via a tube to the spirometer. A peak-flow meter is a simpler device that is similar to the spirometer, and is used in a similar manner. The second technique evaluates lung function by measuring nitric-oxide concentration using a dedicated nitric-oxide monitor. The patient breathes into a mouthpiece connected via a tube to the monitor.

Efficient asthma management requires daily monitoring of respiratory function, which is generally impractical, particularly in non-clinical or home environments. Peak-flow meters and nitric-oxide monitors provide a general indication of the status of lung function. However, these monitoring devices do not possess predictive value, and are used as during-episode markers. In addition, peak-flow meters and nitric-oxide monitors require active participation of the patient, which is difficult to obtain from many children and substantially impossible to obtain from infants.

Congestive heart failure (CHF) is a condition in which the heart is weakened and unable to circulate blood to meet the body's needs. The subsequent buildup of fluids in the legs, kidneys, and lungs characterizes the condition as congestive. The weakening may be associated with either the left, right, or both sides of the heart, with different etiologies and treatments associated with each type. In most cases, it is the left side of the heart which fails, so that it is unable to efficiently pump blood to the systemic circulation. The ensuing fluid congestion of the lungs results in changes in respiration, including alterations in rate and/or pattern, accompanied by increased difficulty in breathing and tachypnea.

Quantification of such abnormal breathing provides a basis for assessing CHF progression. For example, Cheyne-Stokes Respiration (CSR) is a breathing pattern characterized by rhythmic oscillation of tidal volume with regularly recurring periods of alternating apnea and hyperpnea. While CSR may be observed in a number of different pathologies (e.g., encephalitis, cerebral circulatory disturbances, and lesions of the bulbar center of respiration), it has also been recognized as an independent risk factor for worsening heart failure and reduced survival in patients with CHF. In CHF, CSR is associated with frequent awakening that fragments sleep, and with concomitant sympathetic activation, both of which may worsen CHF. Other abnormal breathing patterns may involve prolonged expiration or inspiration, or gradual changes in respiration rate usually leading to tachypnea.

U.S. Pat. No. 5,853,005 to Scanlon, which is incorporated herein by reference, describes a transducer in communication with fluid in a pad. The pad is held in close contact against a sound or movement source, and monitors acoustic signals transferred into the fluid. The signal pattern is monitored aurally and/or compared to predetermined reference patterns, and optional control and stimulation means can be activated in response to the comparison results. The sensed acoustic signal can be transmitted to a remote receiver or processed locally. Typically, the acoustic signal is representative of the heartbeat or breathing of a living organism. The monitoring system may be applied to diverse situations including SIDS, apnea, home baby monitoring, medical transport devices, blood pressure cuffs, seats, combat casualty care and handheld devices. An embodiment is described in which the system is attached to home or institution mattresses for health monitoring, recovery, research, or presence detection.

U.S. Pat. No. 6,666,830 to Lehrman et al., which is incorporated herein by reference, describes a system for detecting the onset of an obstructive sleep apnea event before the obstructive sleep apnea event fully develops, and before the cessation of breathing occurs. The system includes one or more microphones capable of detecting breathing sounds within an airway of a person. The microphones generate signals representative of the breathing sounds, and send the signals to a controller. The controller identifies at least one signal pattern that is associated with a breathing pattern of the person that occurs at the onset of an obstructive sleep apnea event. The controller may also identify at least one signal pattern that is associated with a partially-occluded breathing pattern of the person. The controller identifies the signal patterns by using digital signal processing techniques to analyze the signals representative of breathing sounds. The method involves detecting breathing sounds within an airway of a person, generating signals representative of the breathing sounds, and identifying at least one signal pattern that is associated with a breathing pattern of the person that occurs at the onset of an obstructive sleep apnea event.

U.S. Pat. No. 6,790,183 to Murphy, which is incorporated herein by reference, describes a lung sound diagnostic system for use in collecting, organizing and analyzing lung sounds associated with the inspiration(s) and expiration(s) of a patient. The system includes a plurality of transducers that may be placed at various sites around the patient's chest. The microphones are coupled to signal processing circuitry and A/D converters which digitize the data and preferably provides the digital data to a computer station. The system may also include application programs for detecting and classifying abnormal sounds. The resulting information may be displayed in a variety of formats to facilitate diagnosis. Additionally, the system may include an analysis program for comparing selected criteria corresponding to the detected abnormal sounds with predefined thresholds in order to provide a likely diagnosis. Also described are a system and method for differentiating between the crackles produced by an patient with interstitial pulmonary fibrosis (IPF) from the crackles produced by a CHF patient.

U.S. Pat. No. 6,168,568 to Gavriely, which is incorporated herein by reference, describes a phonopneumograph system for analyzing breath sounds. The system includes a plurality of breath-related sensors placed around the respiratory system of a patient for measuring breath-related activity, and a breath analyzer. The breath analyzer matches the breath sound data produced by the breath-related sensors to a plurality of breath sound templates, each of which parameterizes one type of breath sound, and determines the presence of regular and/or adventitious breath sounds only when the breath sound data matches, within predetermined goodness of fit criteria, one or more of the breath sound templates.

U.S. Pat. No. 6,261,238 to Gavriely, which is incorporated herein by reference, describes a method for analyzing breath sounds produced by a respiratory system. The method includes measuring breath sounds produced by the respiratory system; tentatively identifying a signal as being caused by a breath sound of a given type if it meets a first criterion characteristic of the breath sound of the given type; and confirming the identification if a tentatively identified signal meets a second criterion characteristic of the breath sound of the given type.

U.S. Pat. No. 5,738,102 to Lemelson, which is incorporated herein by reference, describes a system for monitoring and computer analyzing select physiological variables of a patient in real time in order to alert medical personnel to the need for medical treatment or automatically administering such treatment under computer control. Such physiological variables monitored by the system may include lung sounds, respiratory rate and rhythm, heart rate and rhythm, heart sounds, and body temperature. Coded signals relating to the physiological variables are produced and compared with reference versions of same by a decision computer in order to evaluate the patient's condition. If the evaluation indicates medical treatment is needed, the decision computer activates a local and/or a remote alarm to alert medical personnel and/or activates one or more actuators for administering a medical treatment such as the injection or infusion of a drug.

An article by Shochat M et al., entitled, "PedemaTOR: Innovative method for detecting pulmonary edema at the pre-clinical stage," undated, available at http://www.isramed-.info/rsmm_rabinovich/pedemator.htm, which is incorporated herein by reference, describes an impedance monitor for pre-clinical detection of pulmonary edema. The impedance monitor measures "internal thoracic impedance" (ITI), which is roughly equal to lung impedance, by automatically calculating skin-electrode impedance and subtracting it from the measured transthoracic impedance (TTI).

The following articles, which are incorporated herein by reference, may be of interest:

Bentur L et al., "Wheeze monitoring in children for assessment of nocturnal asthma and response to therapy," Eur Respir J 21(4):621-626 (2003).

Stegmaier-Stracca P A et al., "Cough detection using fuzzy classification," Symposium on Applied Computing, Proceedings of the 1995 ACM Symposium on Applied Computing, Nashville, Tenn., United States, pp. 440-444 (1995).

Waris M et al., "A new method for automatic wheeze detection," Technol Health Care 6(1):33-40 (1998).

The inclusion of the foregoing references in this Background section does not imply that they constitute prior art or analogous art with respect to the invention disclosed herein.

SUMMARY OF THE INVENTION

In some embodiments of the present invention, a method for monitoring a chronic medical condition comprises non-invasively monitoring at least one breathing pattern of a subject, typically during sleep at night. The pattern is analyzed in order to (a) predict an approaching clinical episode, such as an asthma attack, and/or (b) monitor the severity and progression of a clinical episode as it occurs. Analyzing the pattern typically comprises comparing the pattern to a baseline pattern. Prediction of an approaching clinical episode facilitates early preventive treatment, which generally reduces the required dosage of medication.

In some embodiments of the present invention, the breathing pattern is monitored by continuously acquiring breathing-related body motion data of the subject during sleep. The motion data is processed to yield at least one periodic breathing-related movement pattern, from which the breathing pattern is extracted. For some applications, the motion data is acquired using a sensing device that does not come in contact with the subject or clothes the subject is wearing. For example, the sensing device may be a pressure gauge, which is typically adapted to be installed under a mattress upon which the subject sleeps. Because the data acquisition is non-invasive (and typically not noticeable), it is generally suitable for monitoring both children and adults in a home environment.

The effectiveness of the techniques described herein is in part based on the observation that some chronic medical conditions interfere with normal breathing during sleep and while awake, resulting in condition-specific abnormal breathing patterns. Various direct and indirect physiological mechanisms modify breathing patterns, resulting in specific patterns related to the cause of modification. Respiratory diseases, such as asthma, chronic obstructive pulmonary disease (COPD), and cystic fibrosis (CF), directly modify breathing patterns, while physiological abnormalities associated with some conditions indirectly modify breathing patterns. For example, such indirect breathing pattern-modifying physiological abnormalities include: (a) congestive heart failure (CHF), which sometimes causes abnormal breathing patterns such as Cheyne-Stokes Respiration (CSR), (b) hypoglycemia, such as caused by diabetes, and (c) abnormal autonomic nervous system activity, such as caused by some neurological conditions.

In some embodiments of the present invention, a system for monitoring chronic medical conditions comprises a breathing-related motion acquisition module, a breathing pattern analysis module, and an output module.

There is therefore provided, in accordance with an embodiment of the present invention, a method for predicting an onset of a clinical episode, including:

sensing breathing of a subject;

determining at least one breathing pattern of the subject responsively to the sensed breathing;

comparing the breathing pattern with a baseline breathing pattern; and predicting the onset of the episode at least in part responsively to the comparison.

For some applications, the breathing pattern includes a breathing rate pattern of the subject, the baseline breathing pattern includes a baseline breathing rate pattern, and comparing the breathing pattern with the baseline breathing pattern includes comparing the breathing rate pattern with the baseline breathing rate pattern.

For some applications, comparing includes determining the baseline breathing pattern by analyzing breathing of the subject during at least one non-symptomatic period. For some applications, comparing includes setting the baseline breathing pattern responsively to a population average breathing pattern.

For some applications, predicting the onset includes predicting the onset responsively to a prolonged inspirium time of the subject, and/or to a prolonged expirium time of the subject. For some applications, the breathing pattern includes successive segments of inspirium and expirium, and predicting the onset includes predicting the onset responsively to a trend towards greater durations of at least one of: the inspirium segments and the expirium segments.

In an embodiment, the clinical episode includes an episode associated with a condition selected from the list consisting of: asthma, chronic obstructive pulmonary disease (COPD), cystic fibrosis (CF), CHF, diabetes, and epilepsy.

In an embodiment, the breathing pattern includes a breathing duty-cycle pattern, and predicting the onset includes predicting the onset responsively to an increase in a breathing duty-cycle of the subject.

For some applications, sensing breathing of the subject includes sensing at least one breathing-related sound selected from the list consisting of: a sound caused by wheezing, and a sound caused by coughing, and predicting the onset includes predicting the onset responsively to an aspect of the breathing-related sound.

For some applications, sensing breathing of the subject includes sensing at least one type of breathing-related mechanical vibrations selected from the list consisting of: mechanical vibrations caused by wheezing, and mechanical vibrations caused by coughing, and predicting the onset includes predicting the onset responsively to an aspect of the breathing-related mechanical vibrations.

In an embodiment, the breathing pattern includes a breathing rate variability pattern, the baseline breathing pattern includes a baseline breathing rate variability pattern, and predicting the onset includes predicting the onset responsively to a decrease in breathing rate variability over time compared to the baseline breathing rate variability pattern. For some applications, determining the at least one breathing pattern includes determining the breathing rate variability pattern and a slow trend breathing rate pattern, comparing the breathing pattern with the baseline breathing pattern includes comparing the breathing rate variability pattern with the baseline breathing rate variability pattern, and comparing the slow trend breathing rate pattern with a baseline slow trend breathing rate pattern, and predicting the onset includes predicting the onset responsively to both comparisons. For some applications, sensing the breathing includes sensing at least one of: breathing sounds of the subject, and respiratory air-flow of the subject. For some applications, the clinical episode includes an asthma attack, and predicting the onset of the episode includes predicting the onset of the asthma attack.

In an embodiment, the breathing pattern and the baseline breathing pattern include respective slow trend breathing rate patterns, and comparing the breathing pattern with the baseline breathing pattern includes comparing the slow trend breathing rate pattern with the baseline slow trend breathing rate pattern. For some applications, the baseline slow trend breathing rate pattern includes a monotonic decline in breathing rate over at least 1 hour, and predicting the onset includes predicting the onset responsively to a difference between the slow trend breathing rate pattern and the monotonic decline in breathing rate.

In an embodiment, sensing the breathing includes acquiring breathing-related body motion data of the subject. For some applications, acquiring the body motion data includes acquiring the body motion data while the subject is sleeping. For some applications, determining the breathing pattern includes analyzing the body motion data to determine a breathing-related movement pattern, and determining the breathing pattern responsively to the breathing-related movement pattern. For some applications, determining the breathing pattern includes removing non-breathing-related motion data from the body motion data. For example, removing the non-breathing-related motion data from the body motion data may include applying analysis techniques such as frequency-domain spectral analysis or time-domain regression analysis.

In an embodiment, acquiring the body motion data includes acquiring the body motion data without contacting the subject or clothes the subject is wearing. For some applications, the clinical episode includes an asthma attack, and predicting the onset of the episode includes predicting the onset of the asthma attack. For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under a mattress upon which the subject lies. Further alternatively or additionally, measuring the pressure includes measuring a pressure under a mattress covering upon which the subject lies, for example, a sheet, a mattress pad, or a mattress cover.

For some applications, the breathing pattern includes a breathing rate variability pattern, the baseline breathing pattern includes a baseline breathing rate variability pattern, and predicting the onset includes predicting the onset responsively to a decrease in breathing rate variability over time compared to the baseline breathing rate variability pattern. For some applications, determining the at least one breathing pattern includes determining the breathing rate variability pattern and a slow trend breathing rate pattern; comparing the breathing pattern with the baseline breathing pattern includes comparing the breathing rate variability pattern with the baseline breathing rate variability pattern, and comparing the slow trend breathing rate pattern with a baseline slow trend breathing rate pattern; and predicting the onset includes predicting the onset responsively to both comparisons.

There is also provided, in accordance with an embodiment of the present invention, a method including:

sensing breathing of a subject during a clinical episode;

determining at least one breathing pattern of the subject responsively to the sensed breathing;

comparing the breathing pattern with a baseline breathing pattern; and assessing a progression of the episode at least in part responsively to the comparison.

For some applications, the breathing pattern includes a breathing rate pattern of the subject, the baseline breathing pattern includes a baseline breathing rate pattern, and comparing the breathing pattern with the baseline breathing pattern includes comparing the breathing rate pattern with the baseline breathing rate pattern.

For some applications, assessing the progression includes assessing the progression responsively to a prolonged inspirium time of the subject, and/or to a prolonged expirium time of the subject.

For some applications, the breathing pattern includes successive segments of inspirium and expirium, and assessing the progression includes assessing the progression responsively to a trend towards greater durations of at least one of: the inspirium segments and the expirium segments.

In an embodiment, the clinical episode includes an episode associated with a condition selected from the list consisting of: asthma, chronic obstructive pulmonary disease (COPD), cystic fibrosis (CF), CHF, diabetes, and epilepsy.

In an embodiment, the breathing pattern includes a breathing duty-cycle pattern, and assessing the progression includes assessing the progression responsively to an increase in a breathing duty-cycle of the subject.

For some applications, sensing breathing of the subject includes sensing at least one breathing-related sound selected from the list consisting of: a sound caused by wheezing, and a sound caused by coughing, and assessing the progression includes assessing the progression responsively to an aspect of the breathing-related sound. For some applications, the clinical episode includes an asthma attack, and assessing the progression includes assessing the progression of the asthma attack responsively to the aspect.

For some applications, sensing breathing of the subject includes sensing at least one type of breathing-related mechanical vibrations selected from the list consisting of: mechanical vibrations caused by wheezing, and mechanical vibrations caused by coughing, and assessing the progression includes assessing the progression responsively to an aspect of the breathing-related mechanical vibrations. For some applications, the clinical episode includes an asthma attack, and assessing the progression includes assessing the progression of the asthma attack responsively to the aspect.

In an embodiment, the breathing pattern includes a breathing rate variability pattern, the baseline breathing pattern includes a baseline breathing rate variability pattern, and assessing the progression includes assessing the progression responsively to a decrease in breathing rate variability over time compared to the baseline breathing rate variability pattern. For some applications, determining the at least one breathing pattern includes determining the breathing rate variability pattern and a slow trend breathing rate pattern; comparing the breathing pattern with the baseline breathing pattern includes comparing the breathing rate variability pattern with the baseline breathing rate variability pattern, and comparing the slow trend breathing rate pattern with a baseline slow trend breathing rate pattern; and assessing the progression includes assessing the progression responsively to both comparisons. For some applications, the clinical episode includes an asthma attack, and assessing the progression of the episode includes assessing a severity of the asthma attack.

In an embodiment, the breathing pattern and the baseline breathing pattern include respective slow trend breathing rate patterns, and comparing the breathing pattern with the baseline breathing pattern includes comparing the slow trend breathing rate pattern with the baseline slow trend breathing rate pattern. For some applications, the baseline slow trend breathing rate pattern includes a monotonic decline in breathing rate over at least 1 hour, and assessing the progression includes assessing the progression responsively to a difference between the slow trend breathing rate pattern and the monotonic decline in breathing rate.

In an embodiment, sensing the breathing includes acquiring breathing-related body motion data of the subject. For some applications, determining the breathing pattern includes analyzing the body motion data to determine a breathing-related movement pattern, and determining the breathing pattern responsively to the breathing-related movement pattern.

In an embodiment, acquiring the body motion data includes acquiring the body motion data without contacting the subject or clothes the subject is wearing. For some applications, the clinical episode includes an asthma attack, and assessing the progression of the episode includes assessing a severity of the asthma attack. For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under a mattress upon which the subject lies. Further alternatively or additionally, measuring the pressure includes measuring a pressure under a mattress covering upon which the subject lies, for example, a sheet, a mattress pad, or a mattress cover.

For some applications, the breathing pattern includes a breathing rate variability pattern, the baseline breathing pattern includes a baseline breathing rate variability pattern, and assessing the progression includes assessing the progression responsively to a decrease in breathing rate variability over time compared to the baseline breathing rate variability pattern. For some applications, determining the at least one breathing pattern includes determining the breathing rate variability pattern and a slow trend breathing rate pattern; comparing the breathing pattern with the baseline breathing pattern includes comparing the breathing rate variability pattern with the baseline breathing rate variability pattern, and comparing the slow trend breathing rate pattern with a baseline slow trend breathing rate pattern; and assessing the progression includes assessing the progression responsively to both comparisons.

There is further provided, in accordance with an embodiment of the present invention, a method including:

sensing breathing of a subject;

determining at least one breathing pattern of the subject responsively to the sensed breathing;

comparing the breathing pattern with a baseline breathing pattern; and detecting an abnormal breathing pattern associated with congestive heart failure (CHF), at least in part responsively to the comparison.

For some applications, determining the breathing pattern includes determining a breathing rate pattern of the subject, and comparing the breathing pattern with the baseline breathing pattern includes comparing the breathing rate pattern with a baseline breathing rate pattern.

For some applications, detecting the abnormal breathing pattern includes detecting Cheyne-Stokes Respiration (CSR), and/or detecting tachypnea.

In an embodiment, sensing the breathing includes acquiring breathing-related body motion data of the subject. For some applications, acquiring the body motion data includes acquiring the body motion data while the subject is sleeping.

In an embodiment, acquiring the body motion data includes acquiring the body motion data without contacting the subject or clothes the subject is wearing. For some applications, detecting the abnormal breathing pattern includes detecting Cheyne-Stokes Respiration (CSR) and/or tachypnea.

For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under a mattress upon which the subject lies. Further alternatively or additionally, measuring the pressure includes measuring a pressure under a mattress covering upon which the subject lies, for example, a sheet, a mattress pad, or a mattress cover.

There is further provided, in accordance with an embodiment of the present invention, a method including:

sensing breathing of a subject;

determining at least one breathing pattern of the subject responsively to the sensed breathing;

comparing the breathing pattern with a baseline breathing pattern; and detecting an abnormal breathing pattern associated with a condition of the subject, at least in part responsively to the comparison, the condition selected from the list consisting of: chronic obstructive pulmonary disease (COPD), cystic fibrosis (CF), diabetes, and epilepsy.

For some applications, determining the breathing pattern includes determining a breathing rate pattern of the subject, and comparing the breathing pattern with the baseline breathing pattern includes comparing the breathing rate pattern with a baseline breathing rate pattern.

In an embodiment, sensing the breathing includes acquiring breathing-related body motion data of the subject. For some applications, acquiring the body motion data includes acquiring the body motion data while the subject is sleeping.

In an embodiment, acquiring the body motion data includes acquiring the body motion data without contacting the subject or clothes the subject is wearing.

For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under a mattress upon which the subject lies. Further alternatively or additionally, measuring the pressure includes measuring a pressure under a mattress covering upon which the subject lies, for example, a sheet, a mattress pad, or a mattress cover.

There is still further provided, in accordance with an embodiment of the present invention, apparatus for predicting an onset of a clinical episode, including:

a breathing sensor, adapted to sense breathing of a subject, and to generate a signal responsively thereto; and a control unit, adapted to:

receive the signal, determine at least one breathing pattern of the subject responsive to the signal, compare the breathing pattern with a baseline breathing pattern, and predict the onset of the episode at least in part responsively to the comparison.

There is additionally provided, in accordance with an embodiment of the present invention, apparatus including:

a breathing sensor, adapted to sense breathing of a subject during a clinical episode, and to generate a signal responsively thereto; and a control unit, adapted to:

receive the signal, determine at least one breathing pattern of the subject responsive to the signal, compare the breathing pattern with a baseline breathing pattern, and assess a progression of the episode at least in part responsively to the comparison.

There is still additionally provided, in accordance with an embodiment of the present invention, apparatus including:

a breathing sensor, adapted to sense breathing of a subject during a clinical episode, and to generate a signal responsively thereto; and a control unit, adapted to:

receive the signal, determine at least one breathing pattern of the subject responsive to the signal, compare the breathing pattern with a baseline breathing pattern, and detect an abnormal breathing pattern associated with congestive heart failure (CHF), at least in part responsively to the comparison.

There is additionally provided, in accordance with an embodiment of the present invention, apparatus including:

a breathing sensor, adapted to sense breathing of a subject during a clinical episode, and to generate a signal responsively thereto; and a control unit, adapted to:

receive the signal, determine at least one breathing pattern of the subject responsive to the signal, compare the breathing pattern with a baseline breathing pattern, and detect an abnormal breathing pattern associated with a condition of the subject, at least in part responsively to the comparison, the condition selected from the list consisting of: chronic obstructive pulmonary disease (COPD), cystic fibrosis (CF), diabetes, and epilepsy.

There is also provided, in accordance with an embodiment of the present invention, a method for clinical episode prediction and assessment, including:

measuring breathing rate variability patterns during night sleep;

comparing said breathing rate variability patterns to normal breathing rate variability patterns; and determining a likelihood of a nearing clinical episode or a progression or severity of an ongoing episode.

For some applications, said measuring of breathing rate variability patterns is executed by means of measurement of a composite body movement signal and extraction of a periodic, breathing-related movement signal from said composite body movement signal. Alternatively, said measuring of breathing rate variability patterns is executed by means of measurement of respiration airflow from a mouth and/or a nose. Further alternatively, said measuring of breathing rate variability patterns is executed by means of acoustic measurement of airway and lung sounds from a chest, a back, a neck, and/or a face.

For some applications, said normal breathing rate patterns are extracted from the patient during non-symptomatic periods. For some applications, the normal breathing rate patterns are extracted from averaged patterns of normal, healthy subjects with similar character of age, height, weight, and/or gender.

For some applications, said breathing rate variability patterns include: (1) cyclic patterns, whose typical durations range from several seconds to several minutes, and/or (2) slow trends of segmented, monotonically declining breathing rate usually lasting several hours.

For some applications, said comparing is based on a calculation of a degree of deviation of said breathing rate variability patterns from said normal breathing rate variability patterns.

In an embodiment, said clinical episode is a clinical asthma episode.

For some applications, said clinical episode relates to any chronic disease affecting breathing rate patterns, such as diabetes, a heart condition, a neurological disorder, or epilepsy.

There is further provided, in accordance with an embodiment of the present invention, apparatus for clinical episode assessment and prediction, including:

a breathing sensor which measures breathing;

an amplifier which amplifies the output signal of the breathing sensor;

an A/D card which digitizes the amplifier output;

a processor, which extracts breathing rate patterns and compares said patterns to normal patterns; and an output device presenting the result on a numerical, textual or graphical display, or transmitting the results to a clinical follow-up center.

For some applications, the breathing sensor is implemented as a motion-sensitive sensor installed under a bed mattress. Alternatively, the breathing sensor is implemented as an airflow detector aimed at a face of the subject. Further alternatively, the breathing sensor is implemented as an acoustic detector aimed or attached to a face, chest, or back of the subject.

The present invention will be more fully understood from the following detailed description of embodiments thereof, taken together with the drawings, in which:

BRIEF DESCRIPTION OF THE DRAWINGS

FIG. 4 is a graph illustrating breathing rate patterns of a chronic asthma patient, measured during an experiment conducted in accordance with an embodiment of the present invention.

DETAILED DESCRIPTION OF EMBODIMENTS

Figure 1:
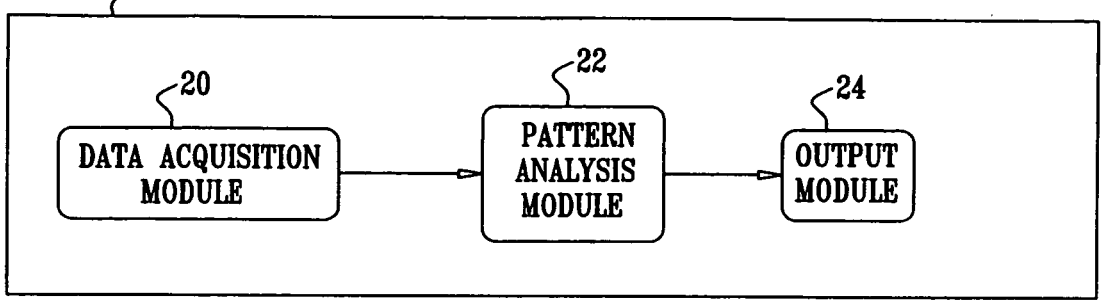
FIG. 1 is a schematic block diagram illustrating a system for monitoring a chronic medical condition, in accordance with an embodiment of the present invention.

FIG. 1 is a schematic block diagram illustrating a system 10 for monitoring a chronic medical condition, in accordance with an embodiment of the present invention. System 10 typically comprises a breathing-related data acquisition module 20, a breathing pattern analysis module 22, and an output module 24. For some applications, two or more of modules 20, 22, and 24 are packaged in a single housing. For other applications, the modules are packaged separately, such as to enable remote analysis by pattern analysis module 22 of breathing signals acquired locally by breathing-related data acquisition module 20.

In an embodiment of the present invention, data acquisition module 20 is adapted to non-invasively monitor breathing patterns of a subject. Pattern analysis module 22 is adapted to analyze the patterns in order to (a) predict an approaching clinical episode, such as an asthma attack, and/or (b) monitor the severity and progression of a clinical episode as it occurs. Output module 24 is adapted to notify the subject and/or a healthcare worker of the predicted or occurring episode. Prediction of an approaching clinical episode facilitates early preventive treatment, which generally reduces the required dosage of medication. When treating asthma, such a reduced dosage generally minimizes the side-effects associated with high dosages typically required to reverse the inflammatory condition once the episode has begun.

Although system 10 may monitor breathing patterns at any time, for some conditions it is generally most effective to monitor such patterns during sleep at night. When the subject is awake, physical and mental activities unrelated to the monitored condition often affect breathing patterns. Such unrelated activities generally have less influence during most night sleep. For some applications, system 10 monitors and records patterns throughout all or a large portion of a night. The resulting data set generally encompasses typical long-term respiratory patterns, and facilitates comprehensive analysis. Additionally, such a large data set enables rejection of segments contaminated with movement or other artifacts, while retaining sufficient data for a statistically significant analysis.

Figure 2:
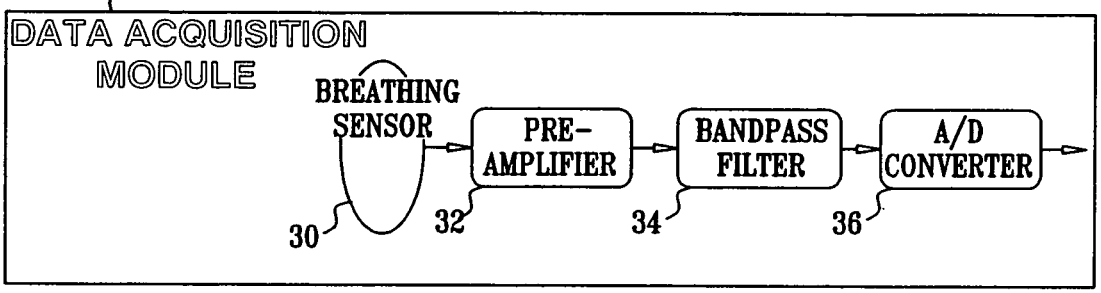
FIG. 2 is a schematic block diagram illustrating a data acquisition module of the system of FIG. 1, in accordance with an embodiment of the present invention.

Reference is now made to FIG. 2, which is a schematic block diagram illustrating data acquisition module 20, in accordance with an embodiment of the present invention. Data acquisition module 20 typically comprises a breathing sensor 30, and other circuitry as appropriate, such as at least one pre-amplifier 32, at least one band-pass filter 34, and an analog-to-digital (A/D) converter 36.

In an embodiment of the present invention, breathing sensor 30 comprises a pressure gauge, which is typically adapted to be installed in, on, or under a mattress upon which the subject sleeps, and to sense breathing-related motion of the subject. For some applications, breathing sensor 30 may be adapted to be installed under a mattress covering upon which the subject sleeps, such as under a sheet, a mattress pad, or a mattress cover. Pattern analysis module 22 is adapted to extract breathing patterns from the motion data, as described hereinbelow with reference to FIG. 3. Alternatively or additionally, breathing sensor 30 comprises another type of sensor, such as an acoustic or air-flow sensor, attached or directed at the subject's face, neck, chest and/or back.

Figure 3:
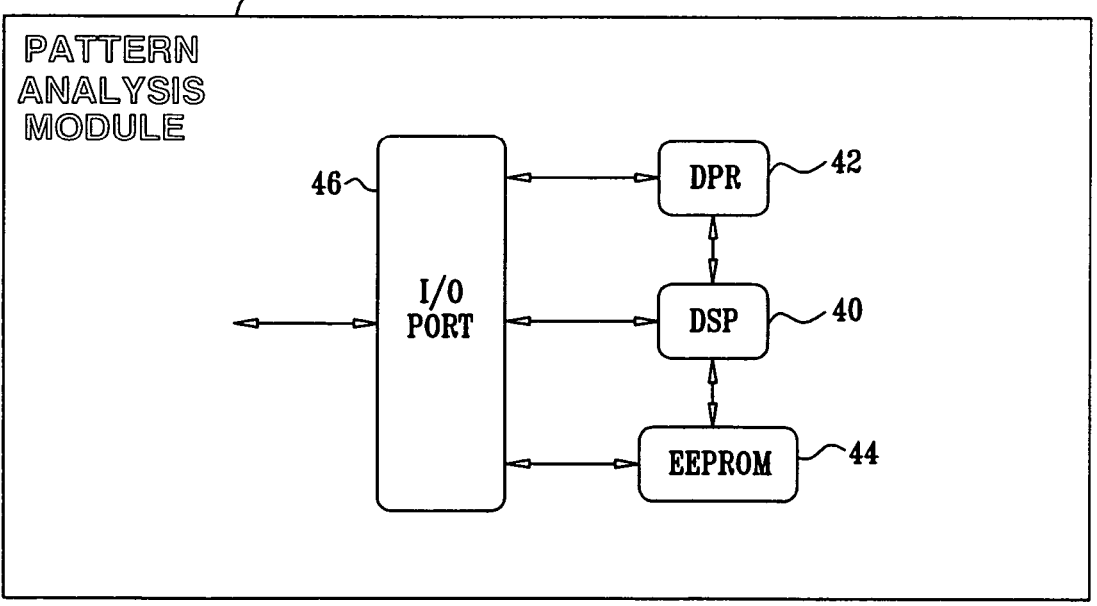
FIG. 3 is a schematic block diagram illustrating a pattern analysis module of the system of FIG. 1, in accordance with an embodiment of the present invention.

FIG. 3 is a schematic block diagram illustrating pattern analysis module 22, in accordance with an embodiment of the present invention. Pattern analysis module 22 typically comprises a digital signal processor (DSP) 40, dual port RAM (DPR) 42, EEPROM 44, and an I/O port 46. Pattern analysis module 22 is adapted to extract breathing patterns from the raw data generated by data acquisition module 20, and to perform processing and classification of the breathing patterns. Pattern analysis module 22 analyzes changes in breathing patterns, typically during sleep. Responsively to the analysis, module 22 (a) predicts an approaching clinical episode, and/or (b) monitors episode severity and progression.

As mentioned above, in an embodiment, breathing sensor 30 comprises a pressure gauge adapted to be installed under a mattress, and to sense breathing-related motion of the subject. Motion of the subject during sleep includes regular breathing movements as well as other, unrelated body movements. In general, breathing-related motion is the dominant contributor to body motion during sleep. Pattern analysis module 22 is adapted to substantially eliminate the portion of the motion signal received from the pressure gauge that represents motion unrelated to breathing. For example, the pattern analysis module may remove segments of the signal contaminated by non-breathing related motion. While breathing-related motion is periodic, non-breathing-related motion is generally random and non-predictable. For some applications, the pattern analysis module eliminates the non-breathing related motion using frequency-domain spectral analysis or time-domain regression analysis. Techniques for applying these analysis techniques will be evident to those skilled in art who have read the present application. For some applications, pattern analysis module 22 uses statistical methods, such as linear prediction or outlier analysis, to remove non-breathing-related motion from the signal. The pattern analysis module typically digitizes the motion data at a sampling rate of at least 10 Hz, although lower frequencies are suitable for some applications.

Pattern analysis module 22 is typically adapted to extract breathing patterns from a train of transient breathing pulses, each pulse including one inhalation-exhalation cycle. Breathing patterns during night sleep generally fall into one of several categories, including:
  relatively fast-changing, random breathing patterns, which occur mainly during REM sleep;
  cyclic breathing rate variability patterns, whose typical duration ranges from several seconds to several minutes;
  slow trends in breathing rates (typically, during normal sleep of a healthy subject, such slow trends include segmented, substantially monotonically declining breathing rates usually lasting several hours; for subjects suffering chronically from certain conditions, such as asthma, the monotonic decline may be less pronounced or absent, as discussed, for example, hereinbelow with reference to FIG. 4);
  interruptions in breathing patterns such as coughing and other sleep disturbances; and
  interruptions in breathing patterns caused by momentary waking.

These breathing patterns are associated with various physiological parameters, such as sleep-stage, anxiety, and body temperature. For example, REM sleep is usually accompanied by randomly variable breathing patterns, while deep sleep stages are usually accompanied by more regular and stable patterns. Abnormally high body temperature may accelerate breathing rate, but usually maintains normal cyclic breathing rate variability patterns. Psychological variables such as anxiety are also modulators of breathing patterns during sleep, yet their effect is normally reduced with sleep progression. Interruptions in breathing patterns such as coughing or that caused by momentary waking may be normal, associated with asthma, or associated with other unrelated pathology, and are assessed in context.

In an embodiment of the present invention, pattern analysis module 22 is configured to predict the onset of an asthma attack, and/or monitor its severity and progression. Module 22 typically analyzes changes in breathing rate and in breathing rate variability patterns in combination to predict the onset of an asthma attack. Although breathing rate typically slightly increases prior to the onset of an attack, this increase alone is not always a specific marker of the onset of an attack. Therefore, in order to more accurately predict the onset of an attack, and monitor the severity and progression of an attack, module 22 typically additionally analyzes changes in breathing rate variability patterns. For some applications, module 22 compares one or more of the following patterns to respective baseline patterns, and interprets a deviation from baseline as indicative of (a) the onset of an attack, and/or (b) the severity of an attack in progress:
  a slow trend breathing rate pattern. Module 22 interprets as indicative of an approaching or progressing attack an increase vs. baseline, for example, for generally healthy subjects, an attenuation of the typical segmented, monotonic decline of breathing rate typically over at least 1 hour, e.g., over at least 2, 3, or 4 hours, or the transformation of this decline into an increasing breathing rate pattern, depending on the severity of the attack;
  a breathing rate variability pattern. Module 22 interprets as indicative of an approaching or progressing attack a decrease in breathing rate variability. Such a decrease generally occurs as the onset of an episode approaches, and intensifies with the progression of shortness of breath during an attack;
  a breathing duty-cycle pattern. Module 22 interprets a substantial increase in the breathing duty-cycle as indicative of an approaching or progressing attack. Breathing duty-cycle patterns include, but are not limited to, inspirium time/total breath cycle time, expirium time/total breath cycle time, and (inspirium+expirium time)/total breath cycle time; and
  interruptions in breathing pattern such as caused by coughs, sleep disturbances, or waking. Module 22 quantifies these events, and determines their relevance to prediction of potential asthma attacks.

Pattern analysis module 22 typically determines baseline patterns by analyzing breathing patterns of the subject during non-symptomatic periods. Alternatively or additionally, module 22 is programmed with baseline patterns based on population averages. For some applications, such population averages are segmented by characteristic traits such as age, height, weight, and gender.

In an embodiment of the present invention, breathing cycles are divided into successive segments of inspirium and expirium. Module 22 interprets as indicative of an approaching or progressing attack a trend towards greater durations of the inspirium and/or expirium segments during sleep (typically night sleep).

In an embodiment of the present invention, breathing sensor 30 further comprises an acoustic sensor for measurement of breathing-related sounds such as those caused by wheezing or coughing. (For some applications, in which breathing sensor 30 comprises a pressure gauge, the acoustic sensor is integrated with the pressure gauge. Alternatively, the acoustic sensor is a separate component.) Pattern analysis module 22 processes such breathing sounds independently, or time-locked to expirium and/or inspirium, e.g., by using spectral averaging to enhance the signal-to-noise ratio of wheezing sounds. For some applications, the level of wheezing and its timing with respect to the timing of inspirium and expirium provides additional information for predicting an upcoming asthma attack and/or monitoring the severity and progression of an attack.

Wheezing and coughing can be attributed to specific parts of the breathing cycle (mainly inspirium and expirium), and thus provide a useful insight regarding the type of upcoming or progressing respiratory distress. In addition, wheezing can be filtered according to the periodicity of the breathing cycle, thus enhancing identification of breathing-related sounds of the obstructed airways. Periodic, breathing-cycle-related wheezing can provide additional insight regarding the type of upcoming or progressing respiratory distress.

In an embodiment of the present invention, pattern analysis module 22 is configured to detect, typically during night sleep, an abnormal breathing pattern associated with congestive heart failure (CHF), such as tachypnea or Cheyne-Stokes Respiration (CSR). Because treatment of CHF appears to be beneficial, its early detection is important.

Reference is again made to FIG. 1. Output module 24 typically comprises a dedicated display unit, such as an LCD or CRT monitor. Alternatively or additionally, the output module comprises a wireless or wired communication port for relaying the acquired and processed data to a remote site for further analysis or interpretation.

Reference is made to FIG. 4, which is a graph illustrating breathing rate patterns of a chronic asthma patient, measured during an experiment conducted in accordance with an embodiment of the present invention. Breathing of the asthma patient was monitored during sleep on several nights. The patient's breathing rate was averaged for each hour of sleep (excluding periods of rapid eye movement (REM) sleep). During the first approximately two months that the patient was monitored, the patient did not experience any episodes of asthma. A line 100 is representative of a typical slow trend breathing pattern recorded during this non-episodic period, and thus represents a baseline slow trend breathing rate pattern for this patient. It should be noted that, unlike the monotonic decline in breathing rate typically observed in non-asthmatic patients, the baseline breathing rate pattern of the chronically asthmatic patient of the experiment reflects an initial decline in breathing rate during the first few hours of sleep, followed by a gradual increase in breathing rate throughout most of the rest of the night.

Line 102 and 104 were recorded on two successive nights at the conclusion of the approximately two-month period, line 102 on the first of these two nights, and line 104 on the second of these two nights. The patient experienced an episode of asthma during the second of these nights. Lines 102 and 104 thus represent a pre-episodic slow trend breathing rate pattern and an episodic slow trend breathing rate pattern, respectively. As can be seen in the graph, the patient's breathing rate was substantially elevated vs. baseline during all hours of the pre-episodic night, and even further elevated vs. baseline during the episodic night.

Using techniques described herein, the pattern of line 102 is compared with the baseline pattern of line 100, in order to predict that the patient may experience an asthmatic episode. The pattern of line 104 is compared with the baseline pattern of line 100 in order to assess a progression of the asthmatic episode.

Although some embodiments described herein relate specifically to asthmatic episodes or CHF, the principles of the present invention may be applied, mutatis mutandis, to predicting and monitoring other respiratory and non-respiratory conditions that affect normal breathing patterns, such as chronic obstructive pulmonary disease (COPD), cystic fibrosis (CF), diabetes, a neurological disorder (e.g., epilepsy), and certain heart diseases in addition to CHF.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
a breathing sensor, configured to:
sense breathing of a subject, by performing at least one type of sensing selected from the group consisting of: (a) sensing the breathing without contacting the subject or clothes the subject is wearing, and (b) sensing the breathing without requiring subject compliance during the sensing, and
generate a signal responsively thereto;
an output module; and
a control unit, configured to:
receive the signal,
determine at least one breathing pattern of the subject having a duration of at least one hour, responsively to the signal,
compare the breathing pattern to a baseline breathing pattern of the subject having a duration of at least one hour,
at least in part responsively to the comparison, evaluate an episode of a condition of the subject, and
drive the output module to generate an output responsively to the evaluation.

2. The apparatus according to claim 1, wherein the breathing pattern includes a breathing rate pattern of the subject, and
wherein the control unit is configured to evaluate the episode responsively to comparing the breathing rate pattern to a baseline breathing rate pattern of the subject.

3. The apparatus according to claim 1, wherein the condition includes chronic obstructive pulmonary disease (COPD), and wherein the control unit is configured to evaluate the episode by evaluating an episode of the COPD.

4. The apparatus according to claim 1, wherein the condition includes cystic fibrosis (CF), and wherein the control unit is configured to evaluate the episode by evaluating an episode of the CF.

5. The apparatus according to claim 1, wherein the condition includes congestive heart failure (CHF), and wherein the control unit is configured to evaluate the episode by evaluating an episode of the CHF.

6. The apparatus according to claim 1, wherein the condition includes epilepsy, and wherein the control unit is configured to evaluate the episode by evaluating an episode of the epilepsy.

7. The apparatus according to claim 1, wherein the breathing sensor comprises an acoustic sensor, configured to sense a breathing-related sound caused by wheezing, and wherein the control unit is configured to evaluate the episode responsively to an aspect of the breathing-related sound.

8. The apparatus according to claim 1, wherein the breathing sensor comprises a motion sensor, configured to sense breathing-related body motion of the subject indicative of the breathing, and wherein the control unit is configured to determine the breathing pattern by:
analyzing the body motion data to determine a breathing-related movement pattern, and
determining the breathing pattern responsively to the breathing-related movement pattern.

9. The apparatus according to claim 1, wherein the condition includes asthma, and wherein the control unit is configured to evaluate the episode by evaluating an episode of the asthma.

10. The apparatus according to claim 9, wherein the breathing sensor is configured to sense the breathing of the subject, by sensing the breathing without requiring subject compliance during the sensing.

11. The apparatus according to claim 9, wherein the breathing sensor is configured to sense the breathing of the subject, by sensing the breathing without contacting the subject or clothes the subject is wearing.

12. The apparatus according to claim 1, wherein the control unit is configured to identify an onset of the episode.

13. The apparatus according to claim 12, wherein the control unit is configured to identify the onset responsively to the breathing pattern and responsively to breathing of the subject during at least one non-symptomatic period.

14. The apparatus according to claim 1, wherein the control unit is configured to monitor a progression of the episode.

15. The apparatus according to claim 1, wherein the control unit is configured to predict an onset of the episode.

16. The apparatus according to claim 1, wherein the baseline breathing pattern is characterized by a segmented, monotonic decline in breathing rate over at least one hour, and wherein the control unit is configured to evaluate the episode by identifying at least one difference between the sensed breathing pattern and the baseline breathing pattern selected from the group consisting of: an attenuation of a decline in the sensed breathing rate pattern vs. the baseline breathing rate pattern, and a transformation of the decline to an increase in the sensed breathing rate pattern vs. the baseline breathing rate pattern.

17. Apparatus comprising:
a sensor, configured to:
sense a cyclic physiological parameter of a subject, generate a signal responsively thereto;
an output module; and
a control unit, configured to:
receive the signal,
analyze the signal to identify a slow trend rate pattern, having a duration of at least one hour,
compare the breathing pattern to a baseline slow trend rate pattern of the physiological parameter of the subject,
at least in part responsively to the comparison, evaluate an episode of a condition of the subject, and
drive the output module to generate an output responsively to the evaluation.

18. The apparatus according to claim 17, wherein the control unit is configured to monitor a progression of an episode of a condition responsively to the comparison.

19. The apparatus according to claim 17, wherein the control unit is configured to detect an episode of a condition responsively to the comparison.

20. The apparatus according to claim 17, wherein the control unit is configured to predict an episode of a condition responsively to the comparison.

21. The apparatus according to claim 17, wherein the control unit is configured to identify that the sensed slow trend rate pattern is characterized by a rate that is greater than rate of the baseline slow trend rate pattern.

22. The apparatus according to claim 17, wherein the sensor is configured to sense breathing of the subject, and wherein the slow trend rate pattern includes a breathing rate pattern.

23. The apparatus according to claim 22, wherein the sensor is configured to sense the breathing by performing at least one type of sensing selected from the group consisting of: (a) sensing the breathing without contacting the subject or clothes the subject is wearing, and (b) sensing the breathing without requiring subject compliance during the sensing.

24. The apparatus according to claim 22, wherein the control unit is configured to identify that the sensed breathing rate pattern is characterized by a breathing rate that is greater than a breathing rate of the baseline breathing rate pattern.

25. The apparatus according to claim 24, wherein the baseline breathing rate pattern is characterized by a segmented, monotonic decline in the breathing rate over at least one hour, and wherein the control unit is configured to evaluate the episode by identifying at least one difference between the sensed breathing rate pattern and the baseline breathing pattern selected from the group consisting of: an attenuation of a decline in the sensed breathing rate pattern vs. the baseline breathing rate pattern, and a transformation of the decline to an increase in the sensed breathing rate pattern vs. the baseline breathing rate pattern.

26. Apparatus comprising:
a breathing sensor, configured to:
sense breathing of a subject, generate a signal responsively thereto;
an output module; and
a control unit, configured to:
receive the signal,
analyze the signal to identify a breathing rate pattern having a duration of at least one hour,
compare the breathing pattern to a baseline breathing pattern of the subject having a duration of at least one hour,
at least in part responsively to the comparison, evaluate an episode of a condition of the subject, and
drive the output module to generate an output responsively to the evaluation.

27. The apparatus according to claim 26, wherein the duration is several hours, and wherein the control unit is configured to analyze the signal to identify the breathing rate pattern having the duration of several hours.

28. The apparatus according to claim 26, wherein the breathing rate pattern includes a cyclic breathing rate variability pattern, and wherein the control unit is configured to analyze the signal to identify the cyclic breathing rate variability pattern.

29. The apparatus according to claim 26, wherein the sensor is configured to sense the breathing by performing at least one type of sensing selected from the group consisting of: (a) sensing the breathing without contacting the subject or clothes the subject is wearing, and (b) sensing the breathing without requiring subject compliance during the sensing.

30. The apparatus according to claim 26, wherein the control unit is configured to monitor a progression of an episode of a condition responsively to the analysis.

31. The apparatus according to claim 26, wherein the control unit is configured to predict an episode of a condition responsively to the analysis.

32. The apparatus according to claim 26, wherein the control unit is configured to detect an episode of a condition responsively to the analysis.

33. The apparatus according to claim 26, wherein the baseline breathing pattern is characterized by a segmented, monotonic decline in breathing rate over at least one hour, and wherein the control unit is configured to evaluate the episode by identifying at least one difference between the sensed breathing pattern and the baseline breathing pattern selected from the group consisting of: an attenuation of a decline in the sensed breathing rate pattern vs. the baseline breathing rate pattern, and a transformation of the decline to an increase in the sensed breathing rate pattern vs. the baseline breathing rate pattern.

34. Apparatus, comprising:

a breathing sensor, configured to:
- sense breathing of a subject, by performing at least one type of sensing selected from the group consisting of: (a) sensing the breathing without contacting the subject or clothes the subject is wearing, and (b) sensing the breathing without requiring subject compliance during the sensing, and
- generate a signal responsively thereto;

an output module; and a control unit, configured to:
- receive the signal,
- determine at least one breathing amplitude pattern of the subject responsively to the signal,
- at least in part responsively to the breathing amplitude pattern, assess a progression of a condition of the subject, and
- drive the output module to generate an output responsively to the assessment.

35. The apparatus according to claim 34, wherein the at least one breathing amplitude pattern includes a Cheyne-Stokes Respiration (CSR) breathing pattern, and wherein the control unit is configured to determine the CSR breathing pattern.

36. The apparatus according to claim 34, wherein the control unit is configured to identify a worsening of the condition responsively to the signal.

* * * * *